United States Patent
Payton et al.

(10) Patent No.: US 10,722,670 B2
(45) Date of Patent: Jul. 28, 2020

(54) PATIENT SPECIFIC AUTO-FLOWRATE CONTROL

(71) Applicant: Fisher & Paykel Healthcare Limited, Auckland (NZ)

(72) Inventors: Matthew Jon Payton, Auckland (NZ); Callum James Thomas Spence, Auckland (NZ); Alicia Jerram Hunter Evans, Auckland (NZ); Andreas Schibler, Auckland (NZ); Craig Karl White, Auckland (NZ); Samantha Dale Oldfield, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 484 days.

(21) Appl. No.: 15/521,874

(22) PCT Filed: Oct. 28, 2015

(86) PCT No.: PCT/NZ2015/050179
§ 371 (c)(1),
(2) Date: Apr. 25, 2017

(87) PCT Pub. No.: WO2016/068725
PCT Pub. Date: May 6, 2016

(65) Prior Publication Data
US 2018/0008791 A1   Jan. 11, 2018

Related U.S. Application Data

(60) Provisional application No. 62/069,760, filed on Oct. 28, 2014.

(51) Int. Cl.
*A61M 16/00* (2006.01)
*A61M 16/16* (2006.01)
(Continued)

(52) U.S. Cl.
CPC ...... *A61M 16/024* (2017.08); *A61M 16/0051* (2013.01); *A61M 16/0069* (2014.02);
(Continued)

(58) Field of Classification Search
CPC ............. A61M 16/00; A61M 16/0003; A61M 16/0051; A61M 16/0057; A61M 16/0066;
(Continued)

(56) References Cited

U.S. PATENT DOCUMENTS 4,602,643 A * 7/1986 Dietz .................. A61B 5/1135
600/534
5,161,525 A    11/1992 Kimm et al.
(Continued)

FOREIGN PATENT DOCUMENTS

WO   WO 2008/146264    12/2008
WO   WO 2013/163687    11/2013

OTHER PUBLICATIONS

International Search Report and Written Opinion for PCT/NZ2015/050179 dated Jan. 29, 2016 in 10 pages.
(Continued)

*Primary Examiner* — Joseph D. Boecker
(74) *Attorney, Agent, or Firm* — Knobbe, Martens, Olson & Bear, LLP (57) ABSTRACT

A respiratory assistance system can provide high flow therapy to patients. The respiratory assistance system can include a patient interface that can deliver a gas flow to a patient and a gas source that can drive the gas flow towards the patient interface at an operating flow rate. The system can include a controller for controlling the operating flow rate of the gas. The controller can apply multiple test flow rate values in a range as the operating flow rate. For each of the test flow rate values, the controller can measure a patient parameter. The controller can determine a new flow rate
(Continued)

value based on the measured patient parameters. Patient parameters can include respiration rate, work of breathing, or any other parameters related to the respiratory circuit.

38 Claims, 8 Drawing Sheets (51) Int. Cl.
*A61M 16/06* (2006.01)
*A61M 16/10* (2006.01)

(52) U.S. Cl.
CPC ........ *A61M 16/0666* (2013.01); *A61M 16/16* (2013.01); *A61M 16/109* (2014.02); *A61M 16/1095* (2014.02); *A61M 2016/003* (2013.01); *A61M 2016/0027* (2013.01); *A61M 2205/3334* (2013.01); *A61M 2205/3344* (2013.01); *A61M 2205/3365* (2013.01); *A61M 2205/3368* (2013.01); *A61M 2205/3375* (2013.01); *A61M 2205/502* (2013.01); *A61M 2205/52* (2013.01); *A61M 2205/581* (2013.01); *A61M 2205/583* (2013.01); *A61M 2230/08* (2013.01); *A61M 2230/42* (2013.01); *A61M 2230/43* (2013.01); *A61M 2230/432* (2013.01); *A61M 2230/50* (2013.01); *A61M 2230/60* (2013.01); *A61M 2230/63* (2013.01)

(58) Field of Classification Search
CPC ............ A61M 16/0069; A61M 16/022; A61M 16/024; A61M 16/06; A61M 16/0666; A61M 16/0672; A61M 16/08; A61M 16/0875; A61M 16/10; A61M 16/109; A61M 16/1095; A61M 16/16; A61M 2016/0027; A61M 2016/003; A61M 2016/0033; A61M 2205/3331; A61M 2205/3334; A61M 2205/3344; A61M 2205/502; A61M 2205/52; A61M 2205/583; A61M 2205/70; A61M 2230/40; A61M 2230/42; A61M 2230/43; A61M 2230/46; A61M 2230/50; A61M 2230/60; A61M 2230/63; A61B 5/08; A61B 5/0816; A61B 5/087

See application file for complete search history.

(56) References Cited

U.S. PATENT DOCUMENTS

| | | | | |
|---|---|---|---|---|
| 6,286,508 | B1* | 9/2001 | Remmers | A61M 16/026 128/204.18 |
| 8,701,665 | B2* | 4/2014 | Tehrani | A61M 16/024 128/204.23 |
| 2006/0225737 | A1* | 10/2006 | Iobbi | A61M 16/0677 128/204.21 |
| 2008/0051674 | A1* | 2/2008 | Davenport | A61B 5/087 600/561 |
| 2008/0190427 | A1* | 8/2008 | Payton | A61M 16/0666 128/203.27 |
| 2008/0243017 | A1* | 10/2008 | Moussavi | A61B 5/087 600/532 |
| 2011/0120462 | A1* | 5/2011 | Tatkov | A61M 16/1075 128/203.14 |
| 2011/0196251 | A1 | 8/2011 | Jourdain et al. | |
| 2011/0290252 | A1* | 12/2011 | Amjad | A61M 16/0051 128/204.23 |
| 2012/0017904 | A1* | 1/2012 | Ratto | A61M 16/0666 128/203.26 |
| 2012/0291783 | A1* | 11/2012 | Peiris | A61M 16/0051 128/204.21 |
| 2017/0043112 | A1* | 2/2017 | Thorgaard | A61J 17/006 |

OTHER PUBLICATIONS

International Preliminary Report on Patentability in corresponding International Patent Application No. PCT/NZ2015/050179, dated May 11, 2017, in 7 pages.

* cited by examiner

FIG. 8 under 37 CFR 1.57.

PATIENT SPECIFIC AUTO-FLOWRATE CONTROL

INCORPORATION BY REFERENCE TO ANY PRIORITY APPLICATIONS

The present application is a national phase of PCT Application No. PCT/NZ2015/050179, filed Oct. 28, 2015, which claims the priority benefit of U.S. Provisional Application No. 62/069,760, filed Oct. 28, 2014, the entirety of which is hereby incorporated by reference herein. Any and all applications for which a foreign or domestic priority claim is identified in the Application Data Sheet as filed with the present application are hereby incorporated by reference under 37 CFR 1.57.

BACKGROUND

A respiratory assistance system including a humidification apparatus may be used to deliver heated and humidified respiratory gases to a patient through a conduit and a patient interface. The respiratory assistance system can provide a number of therapies for patients requiring respiratory support. One of the therapies includes providing a high flow therapy. In high flow therapy, the respiratory support system delivers relatively high flows of gases through an interface, such as an unsealed nasal cannula. The flow rate of gases can be in the range of 5 L/min to 120 L/min for patients.

SUMMARY

Certain aspects, advantages and novel features of the present disclosure are described herein. It is to be understood that not necessarily all such advantages may be achieved in accordance with any particular embodiment of the present disclosure. Thus, the features, aspects, and advantages of the present disclosure may be embodied or carried out in a manner that achieves or selects one advantage or group of advantages as taught herein without necessarily achieving other advantages as may be taught or suggested herein.

In certain embodiments, a respiratory assistance system can include a patient interface that can deliver a gas flow to a patient. The respiratory assistance system can also include a gas source that can drive the gas flow to the patient interface at an operating flow rate. The respiratory assistance system can also include a hardware processor. The hardware processor can apply a plurality of test flow rate values in a range as the operating flow rate. The hardware processor can further measure at least one patient parameter corresponding to each of the plurality of test flow rate values. The hardware processor can also determine a new flow rate value based at least in part on the measured at least one patient parameter. In some embodiments, the hardware processor changes the operating flow rate to the new flow rate value.

The system of the preceding paragraph can have any sub-combination of the following features: wherein the hardware processor can further determine a rate of change in the measured at least one patient parameter as a function of the change in the applied plurality of test flow rate values; wherein said determining the new flow rate further includes determining where in the range of the plurality of test flow rate values does the rate of change approach zero; wherein said determining the new flow rate can further include determining a minimum or a maximum value of the at least one patient parameter measured for each of the plurality of test flow rate values; wherein the at least one patient parameter comprises a respiratory rate and wherein the hardware processor can measure the respiratory rate based at least in part on one or more of the following sensor measurements: pressure fluctuations, flow rate fluctuations, blower fans speed, blower motor power, blower motor torque, expired $CO_2$ fluctuations, transcutaneous $CO_2$ fluctuations, expired patient temperature, EMG signals, Edi signals, impedance pneumography, respiratory inductance plethysmography, acoustic sensing; wherein the at least one patient parameter can include a work of breathing indicator; wherein the patient parameter can include an expiratory $CO_2$ concentration indicator; wherein the patient parameter can include a thoracoabdominal asynchrony indicator; wherein the hardware processor can wait a predetermined time period after the change in the operating flow rate before measuring the patient parameter; wherein the range can include one of the following: 0.5-1.5; 1-2; 1.5-2.5; 2-3; 0.5-4; 1-3; 2-3; and 1-4 (in L/min/kg); wherein the range can include one of the following: 5-120; 5-60; 20-120; 20-60; 60-120; and 50-70 (in L/min) for patients; wherein changing the operating flow rate can include changing an amount of power delivered to the gas source; wherein the gas source can include a blower; wherein the hardware processor can generate an alarm value based at least in part on the measured at least one patient parameter; wherein the hardware processor is can determine that the measured at least one patient parameter is insensitive to the change in flow rate and generate an alarm based on said determination; wherein the patient interface can include any of the following: unsealed nasal cannula, sealed nasal cannula, sealed nasal mask, or a full face mask; wherein the gas source comprises a flow meter, a blender, or a flow mode from a ventilator; and wherein the plurality of test flow rates are applied responsive to a user input.

In some embodiments, a method for delivering gas to a patient can include delivering a gas flow to a patient via a patient interface. The method can further include driving the gas flow from a gas source to the patient interface at an operating flow rate. The method can also include applying a plurality of test flow rate values in a range as the operating flow rate. Further, the method can include measuring at least one patient parameter corresponding to each of the plurality of test flow rate values. The method can further include determining a new flow rate value based at least in part on the measured at least one patient parameter. In some embodiments, the method can include changing the operating flow rate to the new flow rate value.

The method of the preceding paragraph can have any sub-combination of the following features: determining a rate of change in the measured at least one patient parameter as a function of the change in the operating flow rate; determining where in the range of the plurality of test flow rate values that the rate of change approaches zero; wherein the at least one patient parameter can include a respiratory rate; wherein the at least one patient parameter can include a work of breathing indicator; wherein the patient parameter can include a thoracoabdominal asynchrony indicator; wherein the range comprises one of the following: 0.5-1.5; 1-2; 1.5-2.5; 2-3; 0.5-4; 1-3; 2-3; and 1-4 (in L/min/kg); wherein the range can include one of the following: 5-120; 5-60; 20-120; 20-60; 60-120; and 50-70 (in L/min); wherein the patient interface can include any of the following: unsealed nasal cannula, sealed nasal cannula, sealed nasal mask, or a full face mask; wherein said plurality of test flow rate values are received from a user; generating an alarm based on the measured at least one patient parameter; and wherein the gas source comprises any of the following: a blower, a flow meter, a flow mode from a ventilator, and a blender.

BRIEF DESCRIPTION OF THE DRAWINGS

These and other features, aspects, and advantages of the present disclosure will be described with respect to the following figures, which are intended to illustrate and not to limit the preferred embodiments.

DETAILED DESCRIPTION

A respiratory assistance system including a humidification apparatus may be used to deliver heated and humidified respiratory gases to a patient through a conduit and a patient interface. The respiratory assistance system can provide a number of therapies for patients requiring respiratory support. One of the therapies includes providing a high flow therapy. In high flow therapy, the respiratory support system delivers relatively high flows of gases through a nasal interface, which may be unsealed. The flow of gases can be in the range of 5 L/min to 120 L/min. In some embodiments, the flow of gases can be in the range of 10 L/min to 120 L/min. In some embodiments, the flow of gases can be in the range of 20 L/min to 120 L/min. In some embodiments, the flow of gases is in the range of 30 L/Min to 50 L/min. In some embodiments, the flow rate of gases can be as high as 60 L/min. In some embodiments, the flow rate is greater than 60 L/min, but less than 120 L/min. In other embodiments, the flow rate is 120 L/min or higher. The respiration assistance system can adjust the flow rate of gases during the treatment through a control system. A discussion of high flow therapy and how the flow rate can be changed in a respiratory assistance system can be found in PCT Pub. No. WO 2015/033288, titled "Improvements to Flow Therapy", which is hereby incorporated by reference in its entirety.

The flow rate in the high flow therapies may be a function of patient condition and can vary during the treatment. A clinician or patient may not be able to determine the set value of the flow rate for the respiratory assistance system to provide the optimal therapy and comfort. Care providers often do not know proper flow rates for particular patients and tend to set flow rates too low or too high to be clinically optimal. Care provides also often do not know how to gauge the effectiveness of the therapy or how long they should wait to determine effectiveness. Many care providers also may not understand how and when to wean a patient off from high flow therapy.

Accordingly, the present disclosure provides methods and systems for determining an optimal flow rate for a given patient. The methods can be performed by a control system of the device, although certain steps can also be performed by a clinician in communication with the control system. In some embodiments, the respiratory assistance system discussed below includes a control system implemented using a controller for determining a set value for the flow rate. The control system can determine the set value of the flow rate and automatically update it over the time of therapy or based on change in patient conditions. Alternatively, the control system can provide an indication to a clinician to reevaluate the flow rate for the patient or perform one or more other steps to determine a flow rate. Thus, in some embodiments, the control system can advantageously improve the efficacy of the high flow therapy and reduce the probability of the patient requiring more invasive treatment such as invasive mechanical ventilation. A flowrate control method for high flow respiratory therapy may help in a patient spending less time with a flow rate set too high or too low for their immediate breathing support requirements over the course of the therapy.

Flow rate is likely to affect a number of physiological and clinical parameters including work of breathing, end tidal $CO_2$, respiration rate, thoraco-abdominal phase, and other parameters of clinical relevance. In an embodiment, the control system discussed below can generate an indication of the set flow rate for display to a physician. The control system can also automatically change the flow rate. In some embodiments, the control system can warn the clinician if the therapy is not efficacious for the particular patient based on the sensitivity or insensitivity of clinical and physiological parameters to the flow rate. The control system described below can automatically control high flow respiratory therapy flow rates based at least on one or more of the following parameters: respiratory rate, end tidal $CO_2$, thoraco-abdominal asynchrony, and work of breathing.

In some embodiments, the control system's automatic determination of the set value for the flowrate can improve weaning times and reduce hospital lengths of stay. Patients can spend less time at flow rates higher than what is necessary and discontinuation of therapy can be identified earlier. The control system can also assist in faster identification of therapy success or failure. For example, it may be advantageous to know that high flow therapy is not working on a particular patient earlier rather than later. In an embodiment, the control system can compare the physiological parameters of the patient as a function of flow rate to expected predetermined parameters for determining effectiveness of the therapy.

Respiratory Assistance System

Figure 1:
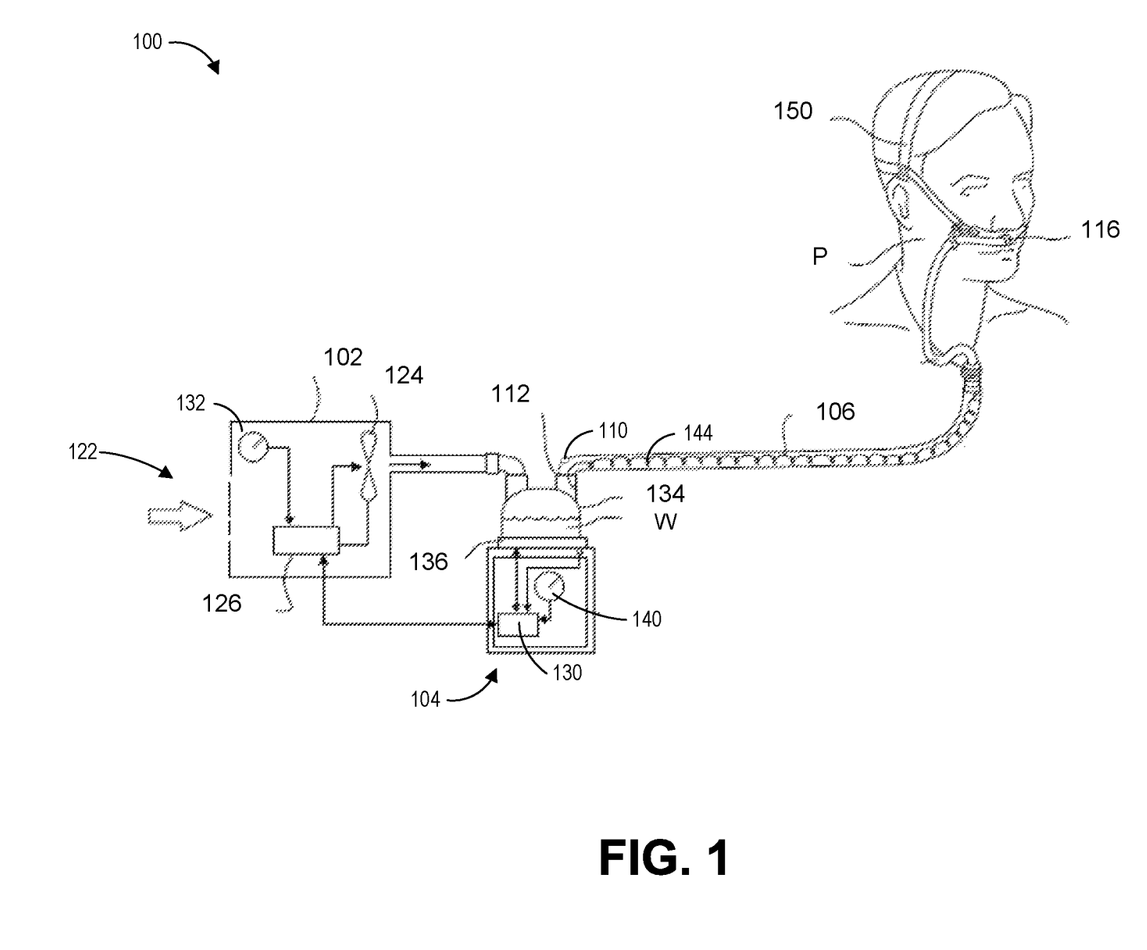
FIG. 1 illustrates a diagram of a respiratory assistance system according to an embodiment of the present disclosure.

FIG. 1 shows a schematic of an example respiratory assistance system 100. As illustrated, the respiratory assistance system 100 includes a humidification apparatus 104, a gases source 102, a patient interface 116, and an inspiratory conduit 106 that can transport respiratory gases from the humidification apparatus 104 to the patient interface 116. The patient interface 116 can include any one of the following interfaces: an unsealed nasal cannula (as shown), sealed nasal cannula, sealed nasal mask, or a full face mask (with, for example, a castle port). Other examples of respiratory systems including nasal cannula are discussed more in detail in PCT Publication WO 2015/33288, titled "Improvements to Flow Therapy", incorporated herein by reference in its entirety. In some embodiments, the gases source 102 and the humidification apparatus 104 may be co-located, within the same housing, and/or comprise a single apparatus. In some embodiments, the humidification apparatus 104 may not be included in the respiratory assistance system 100. Accordingly, gases may flow directly from the gases source 102 to the patient interface 116. In some embodiments, a headgear 150 mechanically supports the patient interface 116 to the patient.

The gases source 102 may include a flow source 124 that can create a flow of respiratory gases to be provided to the humidification apparatus 104. In an embodiment, the flow source 124 is a blower. However, the flow source 124 is not limited to a blower and can include a flow meter, a blender, flow mode from a ventilator, or any other flow generating device. Other flow sources known to those of skill in the art can also be used with any of the embodiments of the present disclosure as further discussed below. In an embodiment, the flow source 124 can include a fan and a motor. In some embodiments, the gases source 102 may comprise an inlet 122 through which ambient air is drawn into the gases source 102. In some embodiments, instead of drawing ambient air, the inlet 122 can be connected to a dry gas source, for example, a gas canister or tank. In some embodiments, the gases source 102 may include a controller 126 that can control the operation of the flow source 124. For example, the controller 126 can execute or implement a control system described more in detail below to control operations of the flow source and the associated flow rate of gases. The control system can, for example in some embodiments that use a blower as a flow source, determine an amount of power delivered to the blower. The fan or motor speed may depend on the amount of power. In some embodiments, the gases source 102 may comprise a user interface 132 configured to provide information regarding user input to the controller 126. The controller 126 may be configured to control the operation of the blower or other flow source 124 based on information provided by the user interface 132 and/or based on other information, for example but not limited to, feedback from the flow source 124, such as from a sensor associated with the flow source 124 as described more in detail below with respect to the control system. The user interface 132 may include buttons, knobs, dials, switches, levers, touch screens, speakers, displays and/or other input or output elements.

As discussed above, the humidification apparatus 104 may be optionally included in the respiratory assistance system 100 but is not necessary in every embodiment. The humidification apparatus 104 may include a humidification chamber 134 and a chamber heater 136. The humidification chamber 134 may be configured to hold a volume of water W or other suitable liquid. The chamber heater 136 may be configured to heat the volume of water W and respiratory gases within the humidification chamber 134, which may increase the temperature of the respiratory gases and may create vapor from the volume of water W that is taken up by the respiratory gases. In some embodiments, the humidification chamber 134 may comprise a chamber inlet (not shown) and a chamber outlet 112. In some embodiments, the inspiratory conduit 106 may be configured to be connected to the chamber outlet 112, such that heated and humidified respiratory gases may be transported by the inspiratory conduit 106 from the humidification chamber 134 to the patient interface 116 and then delivered to a patient P.

In some embodiments, the humidification apparatus 104 may comprise a controller 130 configured to control the operation of the chamber heater 136 and a flow generator, such as the flow source 124. In the embodiments which do not include the humidification apparatus 104, the respiratory assistance system 100 can use controller 126 instead of controller 130. In some embodiments, the humidification apparatus 104 may include a user interface 140 to provide information regarding user input to the controller 130. In some embodiments, the humidification apparatus 104 may include an ambient sensor 146. The ambient sensor 146 may measure a characteristic of the ambient air near the location of the ambient sensor 146, such as a temperature of the ambient air. The controller 130 may receive information regarding a characteristic of the ambient air near the location of the ambient sensor 146 from the ambient sensor 146. The controller 130 or 126 can control the operation of the flow source 124 based on information provided by the user interface 140, based on information provided by physiological sensors, and/or based on other information, for example but not limited to, feedback from the chamber heater 136, such as from a sensor associated with the chamber heater 136. In particular, the controller 130 may be configured to determine an amount of power, or a power duty cycle, to provide to the chamber heater 136 such that the chamber heater 136 delivers a desired amount of heat to respiratory gases and the volume of water W within the humidification chamber 134.

In some embodiments, the respiratory assistance system 100 may include an outlet sensor 110 that is associated with the chamber outlet 112. The outlet sensor 110 may be located at, in, or on the chamber outlet 112, at, in, or on the inspiratory conduit 106 near the connection between the chamber outlet 112 and the inspiratory conduit 106, or at, in, or on another suitable location. The outlet sensor 110 may measure a characteristic of respiratory gases flowing past the location of the outlet sensor 110, such as a temperature of the respiratory gases. The controller 130 may receive information regarding a characteristic of respiratory gases flowing past the location of the outlet sensor 110 from the outlet sensor 110. The controller 130 may be configured to control the operation of the chamber heater 136 based on information provided by the outlet sensor 110, instead of or in addition to other sources of information as previously described.

Control System

Figure 2:
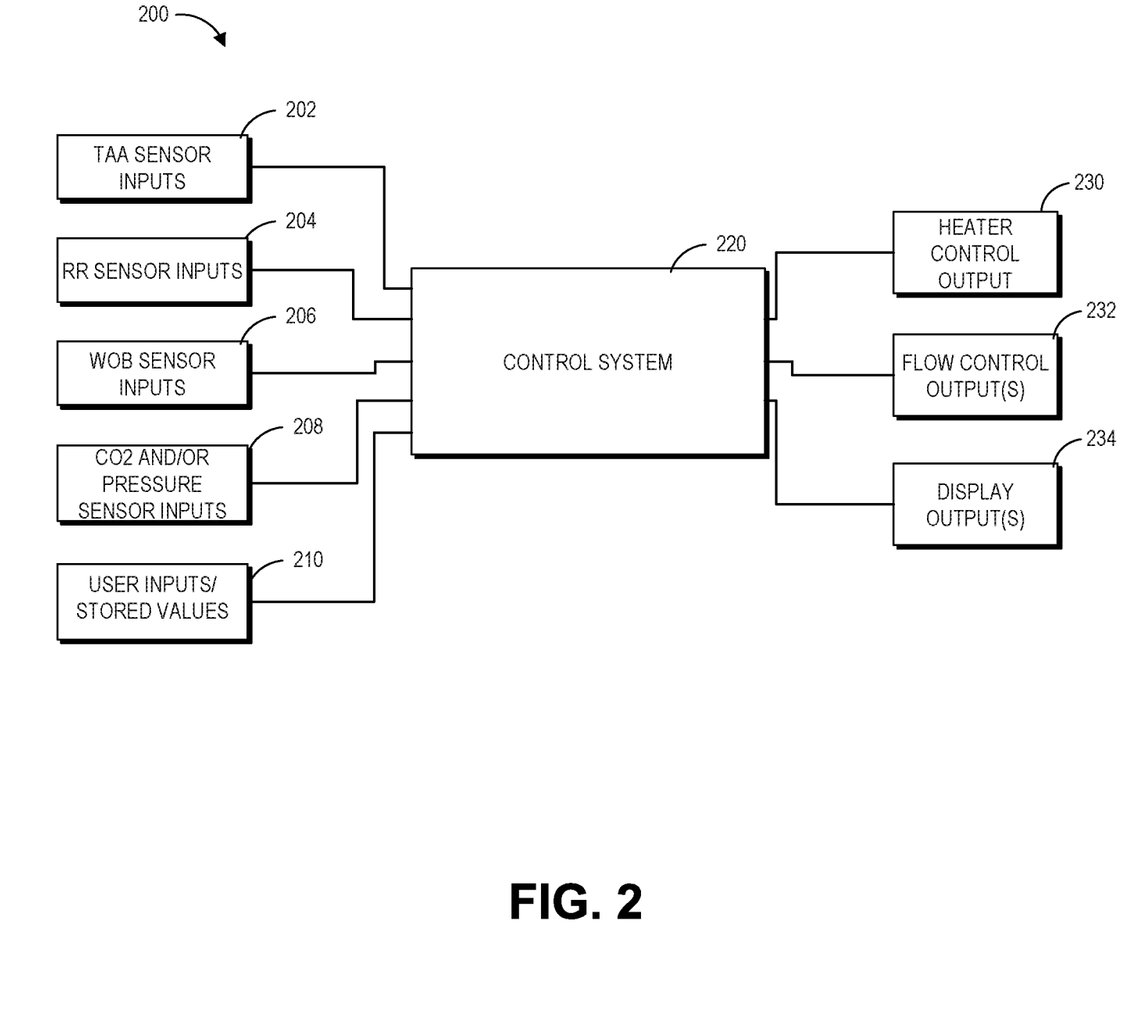
FIG. 2 illustrates a block diagram of a control system interacting with and/or providing control and direction to components of a respiratory assistance system according to an embodiment of the present disclosure.

FIG. 2 illustrates a block diagram of an embodiment of a control system 220 that can detect patient conditions and control operation of the respiratory assistance system 100 including the gas source 124. In an embodiment, the control system 220 manages flow rate 232 of the gas flowing through the respiratory assistance system 100 as it is delivered to a patient. The control system 220 can increase or decrease the flow rate by controlling a motor speed of the blower or a valve in a blender. The control system 220 can automatically determine a set value or a personalized value of the flow rate for a particular patient as discussed below. In some embodiments, the flow rate can be optimized by the control system 220 to improve patient comfort and therapy.

The control system 220 can also generate audio and/or visual outputs 234. For example, the respiratory assistance system 100 can include a display 330 (see FIG. 3) which may further include a speaker. The display 330 can indicate to the physicians any warnings or alarms generated by the control system 220. The display 330 can also indicate control parameters that can be adjusted by the physicians. For example, the control system 220 can automatically recommend a flow rate for a particular patient. The control system 220 can also generate recovery state of the patient and send it to the display.

In some embodiments, the control system 220 can change a temperature set point 230 of one of the heating elements, such as chamber heater 136, to control the output conditions of the gas delivered to the patient. The control system 220 can also change the operation or duty cycle of the heaters described above.

The control system 220 can determine outputs 230-234 based on one or more received inputs 202-210. The inputs 202-208 can correspond to sensor measurements received automatically by the controller 128 or 132. In the illustrated embodiment, the control system 220 receives sensor inputs corresponding to thoraco-abdominal asynchrony (TAA) sensor inputs 202, respiration rate sensor inputs 204, work of breathing sensor inputs 206, and $CO_2$ sensor inputs 208 and or other sensors (pressure sensor, ambient sensor) in the respiratory assistance system 100 described above. In an embodiment, the control system 220 can also receive inputs from user 210 or stored values in a memory 324. The control system 220 can dynamically adjust flow rate 232 for a patient over the time of their therapy. In an embodiment, the control system 220 can continuously detect system parameters and patient parameters.

Thoraco-Abdominal Asynchrony

In a healthy patient, the abdomen and the rib cage move in synchrony when breathing. Thoraco-abdominal asynchrony (TAA) occurs when there is asynchronous movement between the ribcage and abdomen during breathing. Accordingly, TAA is the non-coincident motion of the abdomen and rib cage and can be an indication of respiratory distress. Higher phase difference between the movement of the abdomen and rib cage can indicate a greater level of respiratory distress. In some embodiments, the control system 220 can change the set value of the flow rate of gases to reduce the phase difference. TAA sensor measurements can include measurements from any device or sensors that can detect movement or electrical signal from the abdomen and rib cage. For example, in an embodiment, sensor measurements can include measurements from a respiratory inductance plethysmography or skin mounted strain gauges. Further, the measurements can include electrical activity of the diaphragm and other muscles. This electrical activity can be measured by electromyography (EMG), sEMG, EDI, or electrical impedance tomography (EIT) sensors.

Work of Breathing (WOB)

Work of breathing can correspond to a measure of the effort required to inspire air into the lungs and can be an indication of a number of different breathing disorders. A high work of breathing is uncomfortable for the patient, can lead to elevated CO2 levels, and can result in a patient being escalated to more invasive care such as invasive mechanical ventilation. Therefore, in some embodiments, the control system 220 can determine a flow rate that reduces work of breathing. WOB can be measured as energy in Joules spent by a patient to breath over a minute. WOB may be difficult to detect or measure directly from sensors. Accordingly, in some embodiments, the control system 220 may indirectly measure an indication corresponding to WOB from one or more sensor inputs 206. For example, the control system 220 can indirectly measure WOB from EMG measurements, EDI measurements, respiratory inductance plethysmography (RIP), minute ventilation, expiratory time, pressure-rate product, respiration rate, TAA, pressure-time product or $CO_2$ measurements. EMG can correspond to the magnitude of the electrical signal from the brain to the diaphragm muscles. When the brain signals to breathe more or respiratory distress exists, the EMG signals can increase. RIP measures the movement of the chest wall and/or abdomen and outputs a voltage. Higher voltage can indicate a larger movement of the chest wall and/or abdomen and therefore indicate a higher WOB.

In an embodiment, the control system 220 can store EMG and RIP values across a large group of patients for comparison between a current patient and average values. The control system 220 can determine output parameters based on the average patient values. However, in some instances, patient conditions can vary substantially. Thus, in some embodiments, it may be advantageous to monitor a particular patient to determine output parameters for that patient. For example, the control system 220 can use changes in either EMG or RIP or both to determine whether a change in flow rate increases or decreases WOB. Further, changes in calculated parameters such as minute ventilation, expiratory time, pressure-rate product and/or pressure-time product can also be used to indicate a work of breathing response.

Respiration Rate

Respiratory rate can be an important indicator of patient condition. An abnormal respiratory rate has been shown to be a predictor of serious events such as cardiac arrests and escalation to high levels of care. Respiratory rate can thus provide an indication of deterioration or improvement in patient condition. Respiration rate may also be related to work of breathing.

CO2 Measurements

Patient respiration can also be measured through the use of capnography to determine partial pressure of CO2 in the respiratory gases. The concentration or partial pressure of $CO_2$ in the gas exiting the airway at the end of expiration is called end tidal $CO_2$. Measurement of $CO_2$ (capnography) is common during anaesthesia and intensive care and it is usually presented as a graph of expiratory $CO_2$ plotted against time, or, less commonly, expired volume. The gas expired at the end of expiration can be an indirect but relatively accurate measure of the $CO_2$ partial pressure in arterial blood. Capnography therefore provides information on patient condition, including, for example, $CO_2$ production, lung perfusion, breathing patterns (including respiration rate), alveolar ventilation, and $CO_2$ elimination.

In some embodiments, the control system 220 can use $CO_2$ measurements or indications of $CO_2$ measurements 208 to determine a set value of flow rate 232 for a particular patient. Direct measurements of end tidal $CO_2$ accurately during high flow therapy may be difficult because the cannula flow may dilute and flush the expiratory breath with fresh gas. A method of measuring content of gases from diluted measurements in exhaled breath is described in U.S. Prov. No. 62/046,052 titled "Exhaled Gas Measurement Compensation During High Flow Respiratory Therapy". In some embodiments, the control system 220 can use relative values of $CO_2$ to determine a set value of flow rate as discussed below. The control system 220 can adjust the flow rate to lower the $CO_2$ volume in the expiration. In an embodiment, the control system 220 can adjust the flow rate until changing it any more results in an increase in the lower end tidal $CO_2$ volume. In some embodiments, the control system 220 can adjust the flow rate to maximize end tidal oxygen ($O_2$) volume.

Controller

Figure 3:
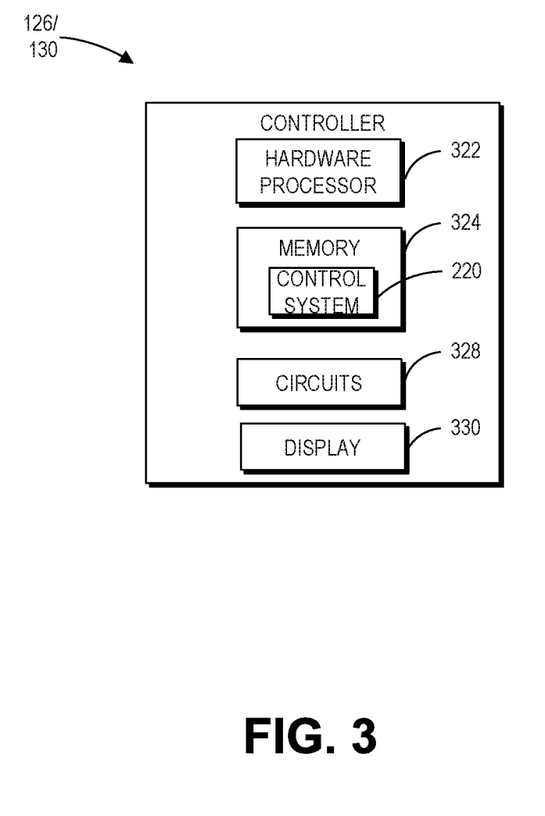
FIG. 3 illustrates a block diagram of a controller according to an embodiment of the present disclosure.

The control system 220 can include programming instructions for detection of input conditions and control of output conditions. The programming instructions can be stored in a memory 324 of the controller 126 and/or 130 as shown in FIG. 3. In some embodiments, the programming instructions correspond to the methods, processes and functions described herein. The control system 220 can be executed by one or more hardware processors 322 of the controller 126 and/or 130. The programming instructions can be implemented in C, C++, JAVA, or any other suitable programming languages. In some embodiments, some or all of the portions of the control system 220 can be implemented in application specific circuitry 328 such as ASICs and FPGAs.

As illustrated in FIG. 2, the control system 220 can receive inputs from multiple components of the respiratory assistance system 100. Not all of the inputs 202-210 shown in FIG. 2 may be present. The inputs 202 to 210 and the outputs 230 to 234 may not necessarily be present in all embodiments. For example, in some embodiments, the control system 220 may only receive the EMG input 206 and generate a flow control measurement 232. Depending on the configuration, some of the components corresponding to the inputs may not be included in the respiratory assistance system 100. Lack of input itself can be used by the control system 220 to determine the input or system conditions.

FIG. 3 illustrates a block diagram of an embodiment of a controller 126 or 132. The controller can include a hardware processor 322 that can execute the instructions stored in a memory 326. In an embodiment, the control system 220 is stored as programming instructions in the memory 326. The controller can also include circuits 328 for receiving sensor signals. The controller can further include a display 330 for transmitting status of the patient and the respiratory assistance system. The display 330 can also show warnings. The controller can also receive inputs from the display.

Patient Parameter Versus Respiratory Assistance System Parameter

Figure 4:
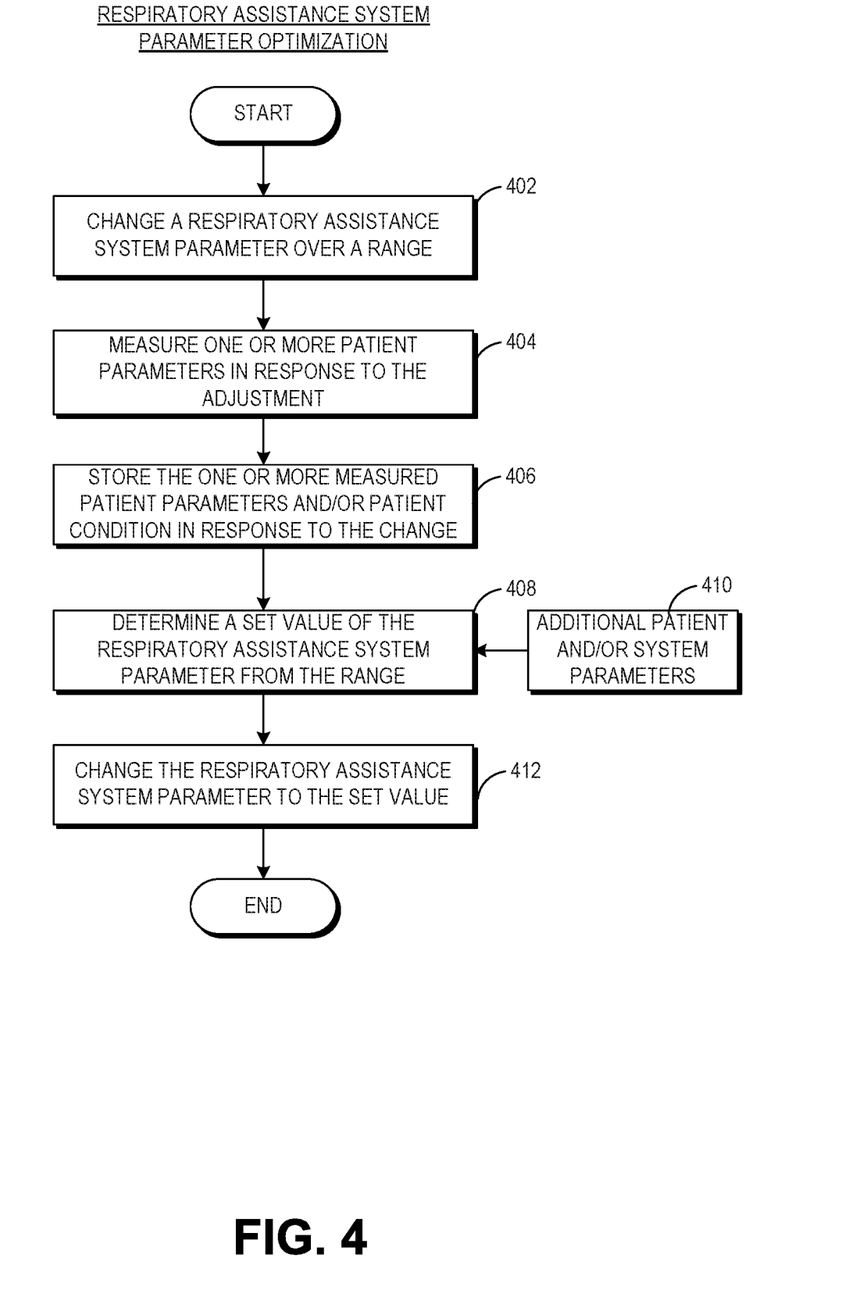
FIG. 4 illustrates a flow chart of a method for respiratory assistance system parameter determination according to an embodiment of the present disclosure.

FIG. 4 illustrates a flow chart of an embodiment of a method 400 for selecting a set value of a parameter of the respiratory assistance system. The parameter can include one or more of heater temperature, flow rate, heating element current. In some embodiments, the set value is selected by the control system 220 to optimize patient comfort and therapy. The method 400 can be implemented by any of the systems described herein. In an embodiment, the method 400 is implemented by the control system 220.

In an embodiment, the method 400 begins at block 402. The control system 220 can adjust a respiratory assistance system parameter over a predetermined range. As discussed above, one of the system parameters adjusted by the control system 220 can include a flow rate parameter. The control system 220 can, for example, increase the motor speed of the blower when a blower is used as the flow source 124 to increase the flow rate of gases through the respiratory assistance system 100. The control system 220 can measure one or more patient conditions in response to the change the system parameter.

In some embodiments, the control system 220 can wait for a predetermined time period before measuring the patient parameter. For example, the control system 220 can wait for the patient to reach steady state before measuring the patient parameter. The wait time can be less than 10 minutes or greater than or equal to 10 minutes. In an embodiment, the control system 220 waits until the patient parameter stops changing significantly after the change in flow rate. The patient parameter can be obtained from one or more sensor measurements discussed above. In an embodiment, the patient parameter is directly obtained from the sensors by the control system 220. In other embodiments, the patient parameter is indirectly deduced or calculated by the control system 220 from the sensor measurements. The patient parameters can include work of breathing, end tidal $CO_2$ volume, respiration rate, phase synchrony, and any other parameters indicating a patient's physiological condition. At block 406, the control system 220 can store the measured patient parameter in the memory. The control system 220 can also store additional parameters of patient and/or system in the memory and associate it with the measured patient parameter. Accordingly, the control system 220 can store the state of the patient and the respiratory assistance system 100 in conjunction with the measured parameter. The control system 220 can adjust the system parameter again and repeat the measurement and storing steps of blocks 404 and 406 respectively. Accordingly, the control system 220 can sweep through the values in a predetermined range for the system parameter and store the corresponding patient parameters in response to the change in the system parameter.

In some embodiments, the control system 220 selectively identifies values within the range. For example, the control system 220 can use a binary search, start from two end points and select in the middle and so on. The control system 220 can also start from previously stored set values and increase or decrease the system parameter from the stored set value. A patient may notice big changes in the system parameters. For example, the patient can notice the big changes in the flow rate. Accordingly, in some embodiments, the control system 220 changes the parameters gradually and may start from the stored set value. The stored set value may also correspond to statistical average over time.

At block 408, the control system 220 can analyse the stored patient parameters as a function of the change in the system parameter. Based on the analysis, the control system 220 can determine a set value for the system parameter. In an embodiment, the control system 220 can determine a derivative of a function corresponding to the stored patient parameter versus system parameter. The control system 220 can determine a point where the derivative of the function is zero. This point can be used as the set value for the patient parameter. Depending on the patient parameter, the point may correspond to either maximum or minimum values of the function. The control system 220 can also determine boundary conditions so that the set value does not fall outside of a predetermined range. In some embodiments, at block 410, the control system 220 can receive additional parameters corresponding to the patient conditions and/or system conditions. Additional parameters may include patient characteristics, such as age, sex, weight, awake or asleep and the like. System parameters may include time of day, type of therapy selected, and the like. The control system 220 can use these additional parameters in determination of the set value.

At block 412, the control system 220 can change the respiratory assistance system parameter to the determined set value. For example, the control system can adjust the flow rate using the process 400 discussed above. The process 400 can, in some embodiments, advantageously optimize system parameters for improved patient comfort and therapy. The control system 220 can run the process 400 periodically to adjust the system parameter. The period may be adjusted by the control system 220 based on changes in the patient condition. For example, a child with bronchitis may go from severe to normal in a matter of days while a patient with a chronic lung disease may need therapy for a month, or indefinitely with gradual improvement or decline and thus gradual adjustments in flow rate. The control system 220 can also run the process 400 in response to detecting a change in the patient condition or system condition. For example, the control system 220 can run the process 400 when the patient falls asleep or wakes up. In some embodiments, the control system 220 can run the process in response to an input from a user, such as a physician or a patient. The control system 220 can run the process until the patient can come off the respiratory assistance system 100.

Work of Breathing Versus Flow Rate

Figure 5:
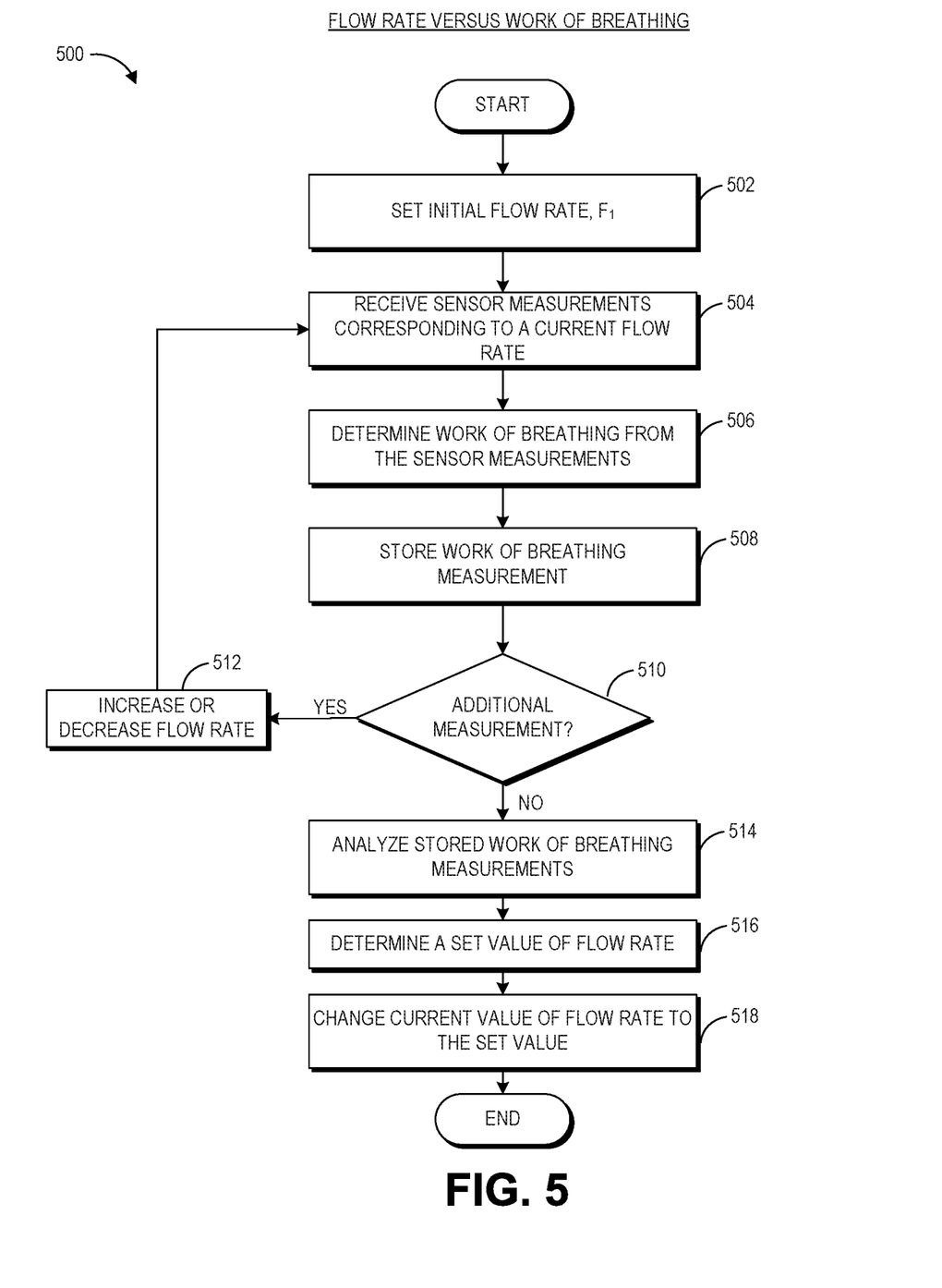
FIG. 5 illustrates a flow chart of a method for determination of flow rate value based on work of breathing according to an embodiment of the present disclosure

FIG. 5 illustrates a flow chart of an embodiment of a process 500 for optimizing flow rate to minimize a patient's work of breathing. The process 500 extends process 400 discussed above for a particular system parameter (flow rate) with respect to a particular patient parameter (work of breathing). Accordingly, some of the discussion above with respect to the process 400 can also apply to process 500. The process 500 can be implemented by any of the systems described herein. In an embodiment, the process 500 is implemented by the control system 220.

The process 500 can begin at block 502 during system initialization. The control system 220 can set the initial flow rate of the respiratory assistance system 100. The initial flow rate may be stored in the memory. The initial flow rate can be a function of the age and/or weight of a patient. For example, in adults, the initial flow rate may be somewhere in the range of 5 to 120 L/min. In an embodiment, the initial flow rate is 30 L/min for an adult patient. For children or neonatal patients, the initial flow rate may be 1 L/min/kg of the child's weight. In some embodiments, the initial flow rate may be greater than 1 L/min/kg, but less than or equal to 3 L/min/kg. In some embodiments, the initial flow rate is greater than 3 L/min/kg. The initial flow rate may also be less than 1 L/min/kg. The initial flow rate can also be received by the control system 220 as a user input. The initial flow rate may be estimated by the control system 220 based on comparing a patient characteristic with predetermined values stored in the memory. As discussed above with respect to the process 400, the process 500 can be initiated by the control system 220 periodically or based on an event. Accordingly, the process 500 can also begin at block 504 for a periodic measurement.

At block 504, the control system 220 can receive sensor measurements to determine the patient's work of breathing corresponding to the current flow rate of the respiratory assistance system 100. The sensor measurements may correspond to electrical signals from EMG probes or NAVA probes attached near the chest of the patient as discussed above. The control system 220 can determine a direct value of work of breathing based on the received sensor measurements at block 506. In some embodiments, the control system 220 does not have to directly or accurately measure the work of breathing. As discussed above, the control system 220 can determine set value from the derivative of a function representing the relationship between the patient parameter and the system parameter. Thus, accurate or direct values may not be necessary as long as the values are relatively comparable. Accordingly, the control system 220 can use voltage measurements from the EMG sensors as a proxy for work of breathing. Since these measurements are from the same patient and the configuration is likely to not change between measurements, it may be advantageous in some embodiments to compare relative measurements as a function of a change in system parameter. Comparing relative measurements may require less processing power. Furthermore, in some embodiments, proxy measurements like voltage or current can be used by the control system 220 instead of directly measuring patient condition.

At block 508, the control system 220 can store work of breathing measurements or the corresponding proxy measurements. The control system 220 can determine if an additional measurement needs to be made at block 510. The determination may be based on whether there are more flow parameters that need to be checked by the control system 220.

For example, in some embodiments applicable to Neonatal patients or children, the control system 220 starts with an initial flow rate of 1 L/min/kg and applies a range of flow rates up to 3 L/min/kg starting from 1 L/min/kg. In some embodiments, the control system 220 can apply any one of the following range of flow rates depending on the patient (in L/min/kg): 0.5-1.5; 1-2; 1.5-2.5; 2-3; 0.5-4; 1-3; 2-3; and 1-4. In some embodiments, the ranges discussed above include the initial or operating flow rate. In some embodiments, the range of flow rates scanned may not include the initial or operating flow rate. The control system 220 can increase the flow rate by 0.5 L/min/kg for each check at block 512. The control system 220 can wait for a predetermined time period before changing the flow rate. The control system 220 can also wait for a predetermined time period after the changing the flow rate and before taking the measurement. Other increments, for example, 0.1, 0.3 or 1, are also possible. Increments may also be a function of patient condition or system parameters. For each increment, the control system 220 can perform steps 504 to 508. When the control system 220 has reached 3 L/min/kg, it can stop the loop and proceed to block 514. In some embodiments, the control system 220 can stop the loop if it determines an increasing or decreasing trend in the patient parameter. For example, the control system 220 can stop the loop when the derivative is zero or close to zero. The derivative can correspond to the rate of change of the patient parameter with respect to the system parameter.

As another example, for an adult patient, the control system 220 can start from 5 L/min and increase from that starting point. The control system 220 can also start from 20 L/min. In an embodiment, the control system 220 can start from a flow rate between 5 L/min and 120 L/min. The control system 220 can increase the flow rates incrementally as discussed above until a predetermined limit or any other condition as discussed above has been satisfied. The predetermined limit can be a flow rate of 120 L/min or lower. In an embodiment, the predetermined limit is 60 L/min. The ranges and the initial rates discussed herein may also be a function of patient characteristics, such as age and weight. In some embodiments, the control system 220 can apply any one of the following range of flow rates (in L/min) for adults: 5-120; 5-60; 20-120; 20-60; 60-120; 30-50; and 50-70. In some embodiments, the ranges discussed above include the initial or operating flow rate. In some embodiments, the range of flow rates scanned may not include the initial or operating flow rate. Further, the flow rate parameters may also depend on a physiological parameter, such as a respiration rate, or the illness. In some embodiments, whether a patient is classified as an adult or a child may depend on age, weight, therapy, or illness. Some children may be classified as adults and administered the adult flow rates depending on their age and/or weight. The flow rates may also be changed by a clinician or a patient using the user interfaces.

Figure 6:
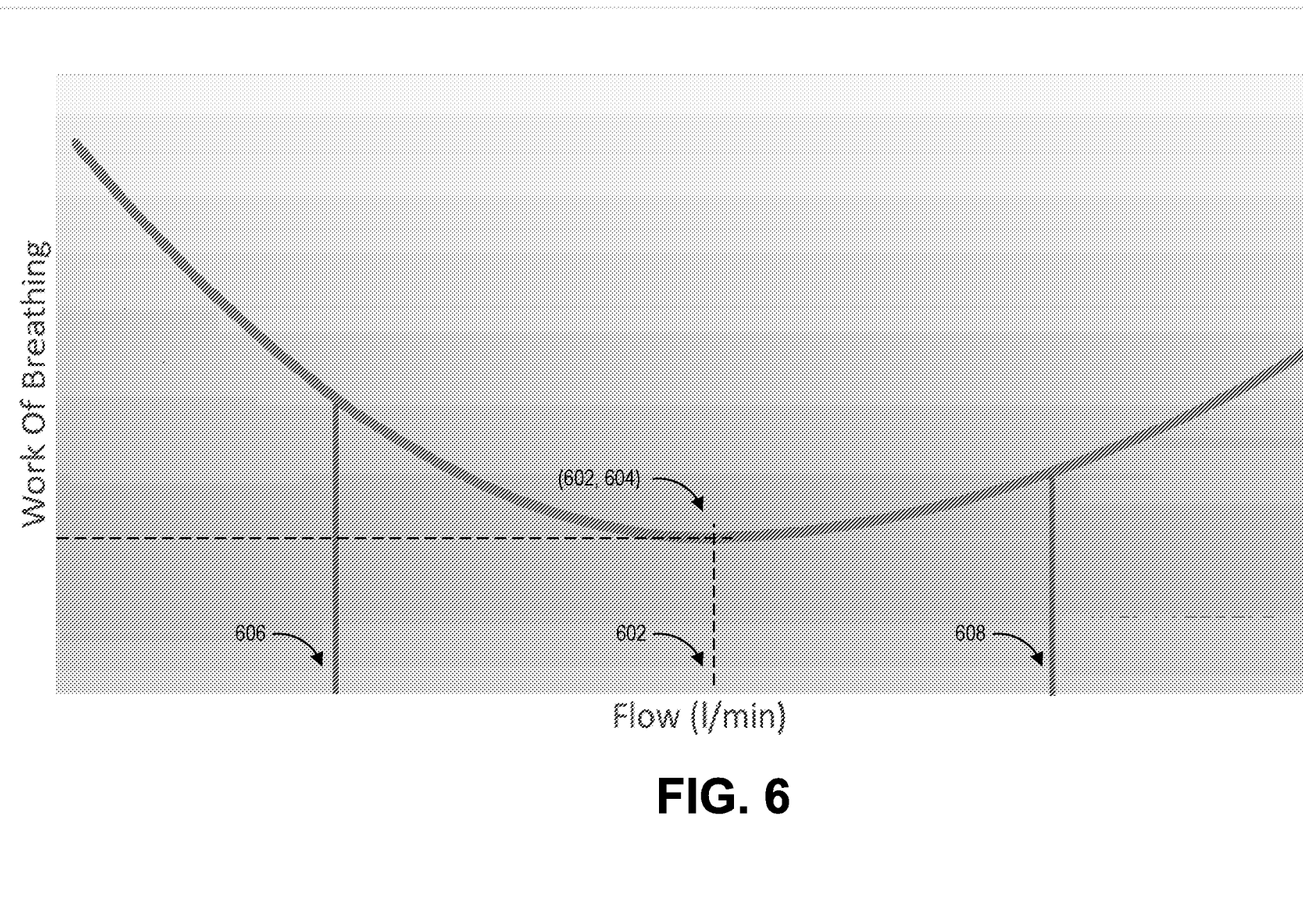
FIG. 6 illustrates an example graph corresponding to measurements of work of breathing indicators versus flow rate according to an embodiment of the present disclosure.

After the control system 220 collects all the patient measurements, it can analyse the measurements at block 514. The control system 220 can select a set value of the flow rate from the measurements by identifying a flow rate with the smallest work of breathing measurement. An example set of collected measurements is illustrated in a graph format in FIG. 6. The control system 220 can select the flow rate 602 corresponding to the minimum point for work of breathing 604 as shown in FIG. 6. The control system 220 can set boundary conditions and not select a flow rate below a minimum rate 606 The control system 220 can also cap flow rate at a maximum rate 608 that may be set by the clinician or stored in the controller. This limit may be based on a flow above which the patient may feel discomfort, for example 120 L/min for adults and 3 L/min/kg for neonatal patients and children. Higher flow rates can also increase noise and pressure. Accordingly, based on the data collected by the control system 220, it can select a set value of the flow rate at block 516. The control system 220 can change the current value of the flow rate to the determined set value at block 518. Accordingly, the control system 220 can optimize flow rate to reduce work of breathing and improve patient comfort. In some embodiments, the control system 220 can reduce work of breathing by 50% by determining a set value for the flow rate particularized for a patient.

Thoraco-Abdominal Asynchrony Versus Flow Rate

Figure 7:
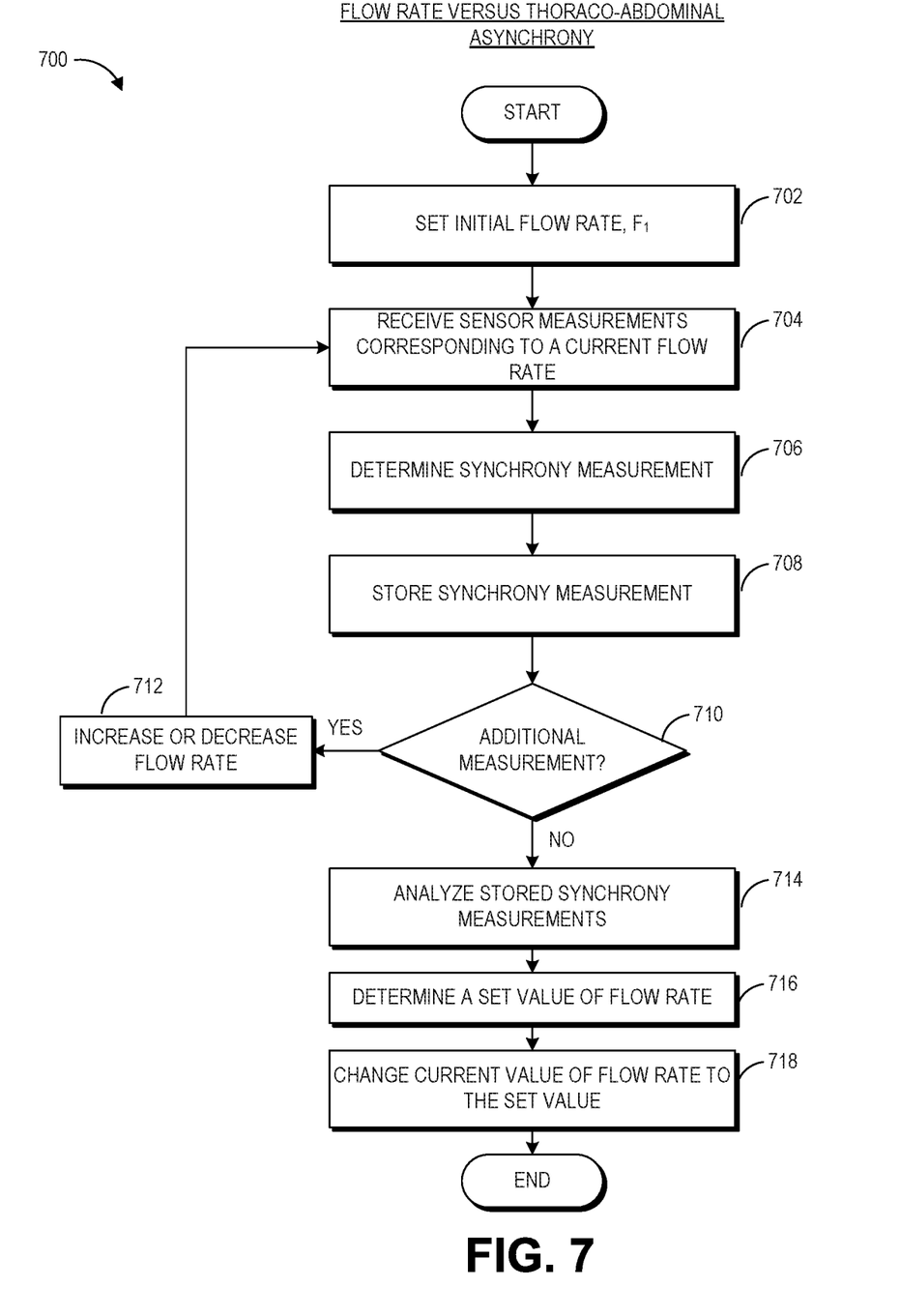
FIG. 7 illustrates a flow chart of a method for determination of flow rate value based on thoraco-abdominal asynchrony according to an embodiment of the present disclosure

FIG. 7 illustrates a flow chart of an embodiment of a process 700 for optimizing flow rate to minimize thoraco-abdominal asynchrony (TAA). The process 700 extends process 400 discussed above for a particular system parameter (flow rate) with respect to a particular patient parameter (TAA). Accordingly, some of the discussion above with respect to the processes 400 and 500 can also apply to the process 700. The process 700 can be implemented by any of the systems described herein. In an embodiment, the process 700 is implemented by the control system 220.

At block 702, the control system 210 can set an initial flow rate. The control system can measure TAA at block 704 for the current flow rate. TAA can correspond to the phase angle between the chest and abdominal motion. As discussed above, the control system 220 can use relative measurements as indications of TAA. Relative measurements can include phase difference in the voltage recorded from the electrodes attached to the different parts of the body of the patient. Accordingly, the control system 220 can receive voltage measurements from sensors at block 704. The control system 220 can identify the phase difference from the voltage measurements between two different sites of the patient's body at block 706. The control system 220 can store the phase difference at block 708 in the memory. The control system 220 can determine if an additional measurement is necessary for a new flow rate at block 710. If necessary, the control system 220 can change the flow rate at block 712 and repeat step 704 to 708. If the control system 220 determines that it does not require additional data, it can proceed to block 714.

The control system 220 can analyse the stored phase measurements at block 714. As discussed above with respect to the work of breathing, the control system 220 can identify a flow rate for which the phase difference is the lowest in the stored measurements. The control system 220 can used the identified value as the set value of the flow rate at block 716. Furthermore, the control system 220 can change the current value of flow rate of the respiratory assistance system 100 to the set value. Accordingly, the process 700 can be used by the control system 220 to optimize flow rate for reduced asynchrony.

Respiration Rate Versus Flow Rate

Figure 8:
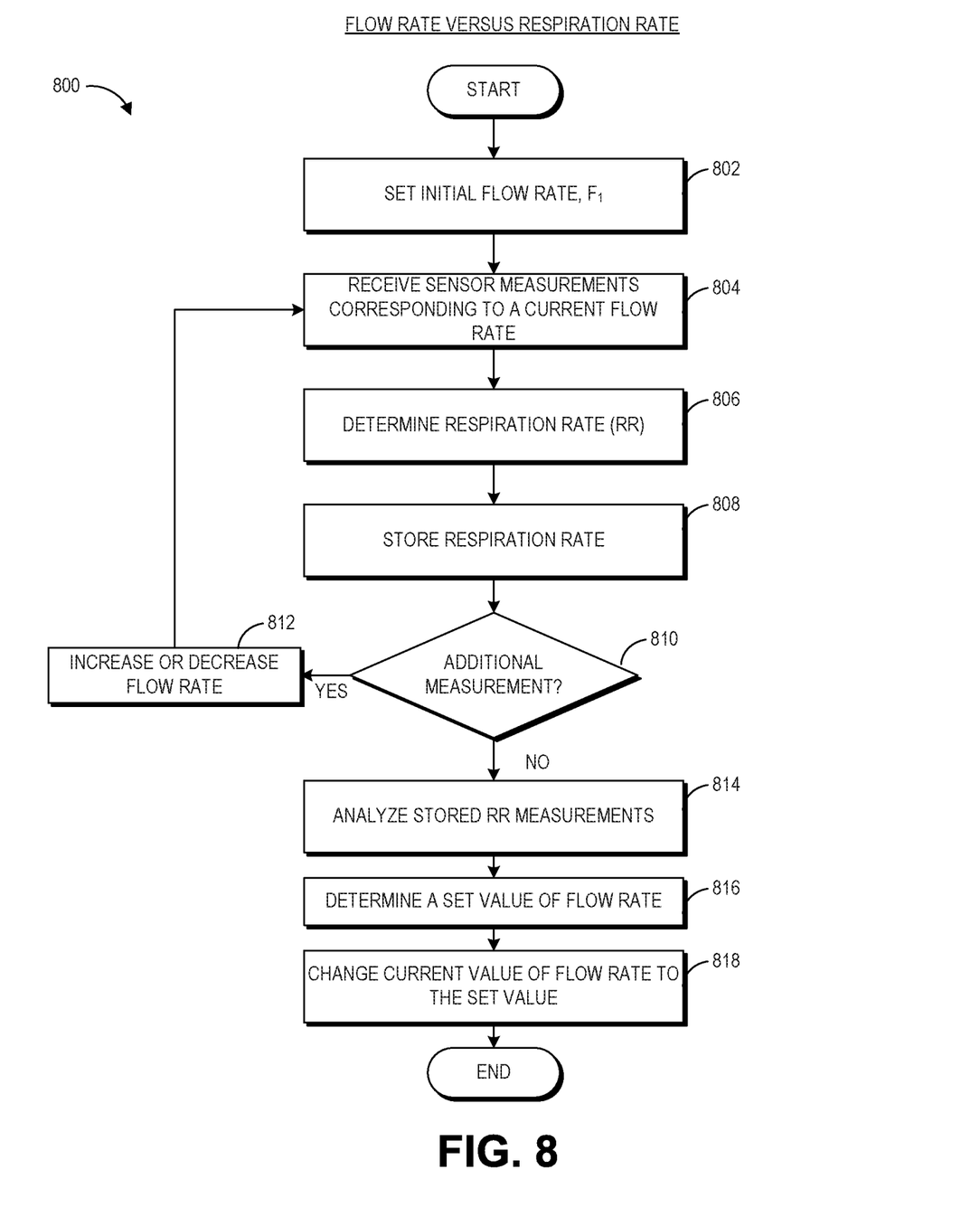
FIG. 8 illustrates a flow chart of a method for determination of flow rate value based on respiration rate according to an embodiment of the present disclosure.

FIG. 8 illustrates a flow chart of an embodiment of a process 800 for optimizing flow rate to respiration rate (RR). The process 800 extends process 400 discussed above for a particular system parameter (flow rate) with respect to a particular patient parameter (RR). Accordingly, some of the discussion above with respect to the processes 400, 500, and 700 can also apply to the process 800. The process 800 can be implemented by any of the systems described herein. In an embodiment, the process 800 is implemented by the control system 220.

Respiration rate can indicate a patient condition or a work of breathing. Accordingly, the control system can use the respiration rate to determine a set value of a system parameter, such as a flow rate. Furthermore, respiration rate is easier to measure than some of the patient parameters discussed above. However, a function corresponding to respiration rate versus flow rate may be substantially monotonic. For example, when the flow rate is continuously increased, the respiration rate correspondingly decreases and heads towards zero. There are clinical situations where it is not desirable for the respiration rate to approach zero. However, the control system 220 can identify a range of flow rates where increasing the flow rate does not decrease the respiration rate. In some embodiments, the control system 220 can identify a section where the rate of change of the respiration rate is reduced.

The process 800 can begin at block 802 with the control system 220 setting an initial flow rate. At block 804, the control system 220 can receive sensor measurements corresponding to respiration rate. In an embodiment, the sensor measurement is a plethysmographic signal. Other measurements for determining respiration rate are discussed above. Respiration rate may also be inputted via a user interface and received by the control system 220. In some embodiments, the control system 220 can determine respiration rate based on the received sensor measurements at block 806. The control system 220 can store the measured respiration rate in the memory at block 808.

The control system 220 can determine if additional measurements of respiration rate are needed with respect to flow rate at block 810. For example, the control system 220 can determine if the current flow rate or the last measured respiration rate is at or exceeded a boundary condition. If the control system 220 determines that additional measurements are needed, then the control system 220 can change the flow rate at block 812 and repeat steps 804 to 808. In the alternative, if the control system 220 determines that additional measurements are not required, the control system 220 can analyse the stored RR measurements at block 814. In some embodiments, the control system 220 can stop additional measurements when the rate of the change of respiration rate with respect to flow rate approaches zero. As discussed above, the control system 220 can use the decrease in the rate of change to determine the set value of the flow rate at block 816. The decrease in the rate of change can correspond to a minimum in work of breathing. Further, the control system 220 can change the current value of the flow rate to the determined set value at block 818.

While the processes 500, 700, and 800 are described separately, the control system 220 can measure multiple physiological parameters at the same time with the change in flow rate. Accordingly, the control system 220 can use a combination of the steps of the processes 500, 700, and 800 to determine a set value of the flow rate. In an embodiment, the control system 220 can average the flow rates determined independently from the different processes.

Warnings

The control system 220 can also generate alarms or warnings based on the measured physiological patient parameters. For instance, if the respiration rate exceeds or drops below an acceptable limit, the control system 220 can generate an alarm for the display. Alternatively the control system can generate alarms or warnings based on relative insensitivity of measured parameters to changes in flow. For example if the work of breathing is insensitive to flow this may indicate that the therapy is less likely to be efficacious. In an embodiment, the control system 220 can change the flow rate and determine that the work of breathing is not affected significantly by the flow rate change. Based on the lack of correlation, the control system 220 can determine that the therapy may not be optimal for the patient.

Applications

The respiratory assistance system 100 with high flow therapy can be used to provide support to patients in emergency rooms, intensive care units (ICU), the operating room (OR), other hospital areas or in-home. In particular, the respiratory assistance system 100 can be used to support a patient under anaesthesia, during preoxygenation and post-operation. Using high flow therapy can have advantages in some embodiments because the patient can still communicate and the mouth is not covered by a mask. Any time a patient requires intubation or endoscopy, the mouth may be blocked and cannot be used for providing invasive air support. Accordingly, high flow therapy along with the nasal cannula configuration of the respiration assistance system 100 can be used in those situations to provide breathing support. The control system 220 can determine work of breathing or other physiological parameters in these cases and automatically determine a set value for flow rate. When patients use the respiratory assistance system 100 in their homes, the control system 220 can be used to adjust the set value of flow rate at the initial stage. The patient can also measure their respiration rate and enter it using the controller.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The disclosed apparatus and systems may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

Depending on the embodiment, certain acts, events, or functions of any of the algorithms, methods, or processes described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially.

It should be noted that various changes and modifications to the presently preferred embodiments described herein will be apparent to those skilled in the art. Such changes and modifications may be made without departing from the spirit and scope of the disclosed apparatus and systems and without diminishing its attendant advantages. For instance, various components may be repositioned as desired. It is therefore intended that such changes and modifications be included within the scope of the disclosed apparatus and systems. Moreover, not all of the features, aspects and advantages are necessarily required to practice the disclosed apparatus and systems. Accordingly, the scope of the disclosed apparatus and systems is intended to be defined only by the claims that follow.

What is claimed is:

1. A respiratory assistance system for delivering gas to a patient, said respiratory assistance system comprising:
   a patient interface configured to deliver a gas flow to a patient;
   a gas source configured to drive the gas flow to the patient interface at an operating flow rate; and
   one or more hardware processors configured to:
      apply a plurality of test flow rate values in a range as the operating flow rate;
      measure at least one patient parameter corresponding to each of the plurality of test flow rate values;
      determine a rate of change in the measured at least one patient parameter as a function of the change in the applied plurality of test flow rate values;
      determine a new flow rate value based at least in part on the measured at least one patient parameter; and
      change the operating flow rate to the new flow rate value.

2. The respiratory assistance system of claim 1, wherein said determining the new flow rate further comprises determining where in the range of the plurality of test flow rate values the rate of change approaches zero.

3. The respiratory assistance system of claim 1, said determining the new flow rate further comprises determining a minimum or a maximum value of the at least one patient parameter measured for each of the plurality of test flow rate values.

4. The respiratory assistance system of claim 1, wherein the at least one patient parameter comprises a respiratory rate and wherein the one or more hardware processors are further configured to measure the respiratory rate based at least in part on one or more of the following sensor measurements: pressure fluctuations, flow rate fluctuations, blower fans speed, blower motor power, blower motor torque, expired $CO_2$ fluctuations, transcutaneous $CO_2$ fluctuations, expired patient temperature, EMG signals, Edi signals, impedance pneumography, respiratory inductance plethysmography, acoustic sensing.

5. The respiratory assistance system of claim 1, wherein the at least one patient parameter comprises one or more of a work of breathing indicator, an expiratory $CO_2$ concentration indicator, or a thoracoabdominal asynchrony indicator.

6. The respiratory assistance system of claim 1, wherein the hardware processor waits a predetermined time period after the change in the operating flow rate before measuring the patient parameter.

7. The respiratory assistance system of claim 1, wherein the range comprises one of the following: 0.5-1.5; 1-2; 1.5-2.5; 2-3; 0.5-4; 1-3; 2-3; or 1-4 (in L/min/kg), or 5-120; 5-60; 20-120; 20-60; 60-120; or 50-70 (in L/min).

8. The respiratory assistance system of claim 1, wherein changing the operating flow rate comprises changing an amount of power delivered to the gas source.

9. The respiratory assistance system of claim 1, wherein the determining the new flow rate comprises minimizing work of breathing of the patient.

10. The respiratory assistance system of claim 1, wherein the hardware processor is further configured to generate an alarm value based at least in part on the measured at least one patient parameter.

11. The respiratory assistance system of claim 1, wherein the hardware processor is further configured to determine that the measured at least one patient parameter is insensitive to the change in flow rate and generate an alarm based on said determination.

12. The respiratory assistance system of claim 1, wherein:
the patient interface is one of unsealed nasal cannula, sealed nasal cannula, sealed nasal mask, or a full face mask;
the gas source comprises a blower, a flow meter, a flow mode from a ventilator, or a blender; or
the respiratory assistance system comprises a humidifier, the humidifier disposed between the patient interface and the gas source, the humidifier configured to humidify gases from the gas source prior to delivery to the patient through the patient interface.

13. The respiratory assistance system of claim 1, wherein the plurality of test flow rates are applied responsive to a user input.

14. The respiratory assistance system of claim 5, wherein the work of breathing indicator comprises a respiration rate of a patient, wherein the respiration rate is indicative of work of breathing and wherein the operating flow rate is selected such that the respiration rate of the patient is minimized or reduced.

15. A respiratory assistance system for delivering gas to a patient, said respiratory assistance system comprising:
a patient interface configured to deliver a gas flow to a patient;
a gas source configured to drive the gas flow to the patient interface at an operating flow rate; and
one or more hardware processors configured to:
apply a plurality of test flow rate values in a range as the operating flow rate;
measure at least one patient parameter corresponding to each of the plurality of test flow rate values, wherein the hardware processor waits a predetermined time period after the change in the operating flow rate before measuring the patient parameter;
determine a new flow rate value based at least in part on the measured at least one patient parameter; and
change the operating flow rate to the new flow rate value.

16. The respiratory assistance system of claim 15, wherein said determining the new flow rate further comprises determining where in the range of the plurality of test flow rate values the rate of change approaches zero.

17. The respiratory assistance system of claim 15, said determining the new flow rate further comprises determining a minimum or a maximum value of the at least one patient parameter measured for each of the plurality of test flow rate values.

18. The respiratory assistance system of claim 15, wherein the at least one patient parameter comprises a respiratory rate and wherein the one or more hardware processors are further configured to measure the respiratory rate based at least in part on one or more of the following sensor measurements: pressure fluctuations, flow rate fluctuations, blower fans speed, blower motor power, blower motor torque, expired CO2 fluctuations, transcutaneous CO2 fluctuations, expired patient temperature, EMG signals, Edi signals, impedance pneumography, respiratory inductance plethysmography, acoustic sensing.

19. The respiratory assistance system of claim 15, wherein the at least one patient parameter comprises one or more of a work of breathing indicator, an expiratory CO2 concentration indicator, or a thoracoabdominal asynchrony indicator.

20. The respiratory assistance system of claim 19, wherein the work of breathing indicator comprises a respiration rate of a patient, wherein the respiration rate is indicative of work of breathing and wherein the operating flow rate is selected such that the respiration rate of the patient is minimized or reduced.

21. The respiratory assistance system of claim 15, wherein the range comprises one of the following: 0.5-1.5; 1-2; 1.5-2.5; 2-3; 0.5-4; 1-3; 2-3; or 1-4 (in L/min/kg), or 5-120; 5-60; 20-120; 20-60; 60-120; or 50-70 (in L/min).

22. The respiratory assistance system of claim 15, wherein changing the operating flow rate comprises changing an amount of power delivered to the gas source.

23. The respiratory assistance system of claim 15, wherein the determining the new flow rate comprises minimizing work of breathing of the patient.

24. The respiratory assistance system of claim 15, wherein the hardware processor is further configured to generate an alarm value based at least in part on the measured at least one patient parameter.

25. The respiratory assistance system of claim 15, wherein the hardware processor is further configured to determine that the measured at least one patient parameter is insensitive to the change in flow rate and generate an alarm based on said determination.

26. The respiratory assistance system of claim 15, wherein:
the patient interface is one of unsealed nasal cannula, sealed nasal cannula, sealed nasal mask, or a full face mask;
the gas source comprises a blower, a flow meter, a flow mode from a ventilator, or a blender; or
the respiratory assistance system comprises a humidifier, the humidifier disposed between the patient interface and the gas source, the humidifier configured to humidify gases from the gas source prior to delivery to the patient through the patient interface.

27. The respiratory assistance system of claim 15, wherein the plurality of test flow rates are applied responsive to a user input.

28. A respiratory assistance system for delivering gas to a patient, said respiratory assistance system comprising:
a patient interface configured to deliver a gas flow to a patient;
a gas source configured to drive the gas flow to the patient interface at an operating flow rate; and
one or more hardware processors configured to:
apply a plurality of test flow rate values in a range as the operating flow rate;
measure at least one patient parameter corresponding to each of the plurality of test flow rate values;
determine that the measured at least one patient parameter is insensitive to the change in flow rate and generate an alarm based on said determination;
determine a new flow rate value based at least in part on the measured at least one patient parameter; and
change the operating flow rate to the new flow rate value.

29. The respiratory assistance system of claim 28, wherein said determining the new flow rate further comprises determining where in the range of the plurality of test flow rate values the rate of change approaches zero.

30. The respiratory assistance system of claim 28, said determining the new flow rate further comprises determining a minimum or a maximum value of the at least one patient parameter measured for each of the plurality of test flow rate values.

31. The respiratory assistance system of claim 28, wherein the at least one patient parameter comprises a respiratory rate and wherein the one or more hardware processors are further configured to measure the respiratory rate based at least in part on one or more of the following sensor measurements: pressure fluctuations, flow rate fluctuations, blower fans speed, blower motor power, blower motor torque, expired CO2 fluctuations, transcutaneous CO2 fluctuations, expired patient temperature, EMG signals, Edi signals, impedance pneumography, respiratory inductance plethysmography, acoustic sensing.

32. The respiratory assistance system of claim 28, wherein the at least one patient parameter comprises one or more of a work of breathing indicator, an expiratory CO2 concentration indicator, or a thoracoabdominal asynchrony indicator.

33. The respiratory assistance system of claim 32, wherein the work of breathing indicator comprises a respiration rate of a patient, wherein the respiration rate is indicative of work of breathing and wherein the operating flow rate is selected such that the respiration rate of the patient is minimized or reduced.

34. The respiratory assistance system of claim 28, wherein the range comprises one of the following: 0.5-1.5; 1-2; 1.5-2.5; 2-3; 0.5-4; 1-3; 2-3; or 1-4 (in L/min/kg), or 5-120; 5-60; 20-120; 20-60; 60-120; or 50-70 (in L/min).

35. The respiratory assistance system of claim 28, wherein changing the operating flow rate comprises changing an amount of power delivered to the gas source.

36. The respiratory assistance system of claim 28, wherein the determining the new flow rate comprises minimizing work of breathing of the patient.

37. The respiratory assistance system of claim 28, wherein:
  the patient interface is one of unsealed nasal cannula, sealed nasal cannula, sealed nasal mask, or a full face mask;
  the gas source comprises a blower, a flow meter, a flow mode from a ventilator, or a blender; or
  the respiratory assistance system comprises a humidifier, the humidifier disposed between the patient interface and the gas source, the humidifier configured to humidify gases from the gas source prior to delivery to the patient through the patient interface.

38. The respiratory assistance system of claim 28, wherein the plurality of test flow rates are applied responsive to a user input.

* * * * *